United States Patent [19]

Kaiser et al.

[11] 4,024,184

[45] May 17, 1977

[54] PREPARATION OF N-(2-ALKOXYETHYL)ALKANAMIDES AND 2-ALKOXYETHYL AMINES FROM 2-OXAZOLINES

[75] Inventors: Mark E. Kaiser; Peter W. Owen, both of Midland, Mich.

[73] Assignee: The Dow Chemical Company, Midland, Mich.

[22] Filed: May 21, 1976

[21] Appl. No.: 698,446

[52] U.S. Cl. .................. 260/561 R; 260/307 F; 260/584 C
[51] Int. Cl.² ............... C07C 102/00; C07C 85/00
[58] Field of Search ........ 260/561 R, 307 F, 584 C

[56] References Cited

UNITED STATES PATENTS

| 2,048,821 | 7/1936 | Schneider | 260/561 R |
|---|---|---|---|
| 2,416,552 | 2/1947 | Valku | 260/561 R |

OTHER PUBLICATIONS

Krabbe et al., Chem. Bencht., 73 (1940), pp. 657–661.
Frump, Chemical Reviews, 71 (1971), pp. 494–495, 497–498.

Primary Examiner—Arthur P. Demers
Attorney, Agent, or Firm—James B. Guffey

[57] ABSTRACT

N-(2-alkoxyethyl)alkanamides, such as N-(2-ethoxyethyl)ethanamide and N-(2-methoxyethyl)propanamide, are prepared by reacting a 2-oxazoline with methanol or ethanol in the presence of a strong base, such as sodium methoxide. Subsequent hydrolysis of such amides provides a convenient means for obtaining 2-alkoxyethyl amines.

12 Claims, No Drawings

PREPARATION OF N-(2-ALKOXYETHYL)ALKANAMIDES AND 2-ALKOXYETHYL AMINES FROM 2-OXAZOLINES

BACKGROUND OF THE INVENTION

This invention relates to processes for the preparation of amido ethers and amino ethers by reaction of 2-oxazolines with alkanols. For a discussion of various known reactions of oxazolines see "Oxazolines. Their Preparation, Reactions, and Applications," John A. Frump, Chemical Reviews, Vol. 71, No. 5, pp. 483–505 (1971).

It is known that 2-alkoxyethyl amines can be prepared by reacting aziridines with alkanols under acidic conditions. Dermer and Ham, ETHYLENIMINE AND OTHER AZIRIDINES, Academic Press, pp. 224–6 (1969). It is also known that the corresponding N-(2-alkoxyethyl)alkanamides can be prepared by reacting such amines with alkanoyl chlorides. Morrison and Boyd, ORGANIC CHEMISTRY, 2nd ed., Allyn and Bacon, Inc., pp. 751–3 (1966).

SUMMARY OF THE INVENTION

This invention comprises a new process for the preparation of amido ethers and new processes for the preparation of amino ethers.

The new process for amido ether preparation is represented by the following equation:

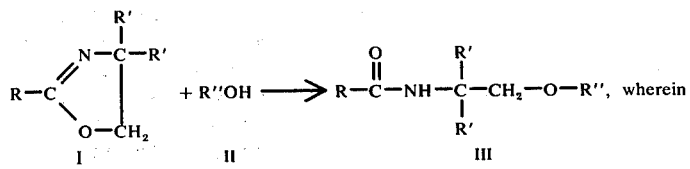

R is hydrogen or an alkyl radical containing from 1 to about 17 carbon atoms, each R' independently is hydrogen, methyl or ethyl and R" is methyl or ethyl.

This novel process comprises reacting by contacting, in liquid phase, an oxazoline (I) with methanol or ethanol (preferably methanol) in the presence of a catalytic amount of an alkali metal or derivative thereof.

To the best of our knowledge, reactions between 2-oxazolines and alkanols were unknown prior to our discovery.

The corresponding free amino ether (i.e., NH$_2$—C(-R')$_2$—CH$_2$—O—R") is prepared as a byproduct when the above process is conducted using excess alkanol. Alternatively, those amines are prepared by subsequent hydrolysis of the amido ether.

The above described amido ethers (III) are useful as intermediates for the preparation of the corresponding amino ethers.

The free amino ethers are useful acid scavengers and epoxy resin curing agents. For a discussion of the use of primary amines as epoxy resin curing agents, see HANDBOOK OF EPOXY RESINS, Lee and Neville, McGraw-Hill Book Company, Chapter 5 (1967). In addition such free amino ethers are useful as chemical intermediates for mining chemicals and for biocides for cutting oil preservation.

DETAILED DESCRIPTION OF THE INVENTION

This invention is a process for preparing amido ethers by contacting, in liquid phase, an oxazoline with methanol or ethanol (preferably methanol) in the presence of a catalytic amount of an alkali metal or derivative thereof.

The oxazolines useful in the practice of this invention are 2-oxazolines of the formula

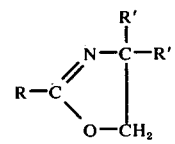

wherein R is hydrogen or alkyl of from 1 to about 17 carbon atoms, preferably hydrogen, methyl or ethyl, most preferably methyl or ethyl; and each R' independently is hydrogen, methyl or ethyl, preferably hydrogen. The compounds represented by I form a known class of compounds. Illustrative members of this class include: 2-methyl-, 2-ethyl-, 2-propyl-, 2-hexyl-, 2-nonyl-, 2-undecyl-, 2-heptadecyl- 2-oxazoline, the corresponding 4-methyl-2-oxazolines, 4-ethyl-2-oxazolines, 4,4-dimethyl-2-oxazolines, and the like.

2-Methyl- and 2-ethyl-2-oxazoline are the most preferred oxazoline reactants.

The alkali metals and derivatives thereof (i.e., catalysts) useful in the practice of the invention include lithium, sodium, potassium, rubidium, cesium, francium (preferably lithium, sodium and potassium) and derivatives thereof corresponding to the formula M$^+$$^-$OR'" wherein M is selected from the aforementioned group of alkali metals and R'" is hydrogen or alkyl of from 1 to about 4 carbon atoms, preferably R'" is methyl or ethyl.

Methoxides and ethoxides of lithium, sodium and potassium are the most preferred catalysts.

The catalyst is employed in the reaction in a small but catalytic amount, i.e. an amount sufficient to provide a measurable increase in the rate of reaction. The exact amount of catalyst can vary depending upon the reaction rate desired and the catalyst used. However, as a general rule, a satisfactory reaction rate is achieved when the catalyst is used in amounts between about 1 and about 50, preferably between about 10 and about 30, mole percent of the catalyst, based on the moles of oxazoline initially present.

The ratio of reactants (i.e., alkanol to 2-oxazoline ratio) may vary. However, the stoichiometry of the reaction makes it desirable that at least equimolar amounts of alkanol be used based upon the 2-oxazoline reactant. Naturally more than equimolar amounts of the alkanol may be employed. For example, utilization of excess alkanol is often advantageous in terms of increased reaction rates, improved yields, improved mixing, better heat transfer, and the like. Furthermore conducting the reaction in the presence of excess alkanol for prolonged durations (i.e., after the point at which no significant further increase in the amido ether product concentration is observed) results in the production of the corresponding amino ether as a reaction by-product; thus providing a convenient new means for preparing such amino ethers from 2-oxazolines.

The reaction temperature employed in the practice of the invention can be varied but convenient rates of reaction have been observed at reaction temperatures between about 100° C and about 225° C (preferably between about 150° C and about 170° C). At these temperatures, superatmospheric or autogenous pressure is generally employed to retain the reactants in the liquid phase.

The invention is preferably practiced under essentially anhydrous conditions. However, the total absence of water from the reaction mixture is not essential. Thus, for example, water introduced into the reaction mixture, whether as a contaminant of one or more of the reactants or as a by-product of the formation in situ of alkali metal methoxide or ethoxide from an alkali metal hydroxide and methanol or ethanol respectively, is not fatal to the successful practice of the invention. However, water present during the reaction serves to reduce the yield of the desired product by hydrolyzing approximately an equimolar amount of the 2-oxazoline reactant. It is therefore desirable that the water content of the reaction mixture be maintained as low as is practical.

The practice of the invention is further illustrated by the following examples.

Example 1

Preparation of N-(2-methoxyethyl)ethanamide from 2-Methyl-2-oxazoline and Methanol in the Presence of Sodium Methoxide.

In a one-liter stainless steel Parr bomb, 170 g (2 moles) of 2-methyl-2-oxazoline is mixed with 64 g (2 moles) anhydrous methanol. To this mixture is added a 13.5 g portion (0.25 mole) of sodium methoxide. The bomb is sealed and heated, with stirring, to 160° C for a period of 23 hours. The bomb is cooled and opened and the contents are suction-filtered through a glass fritted funnel, removing 16.3 g of previously suspended solid. This solid is washed with acetone and the washings are added to the filtrate.

The dark brown clear filtrate is vacuum distilled using a five-plate Oldershaw column equipped with a cold-finger condenser to give a light yellow, clear distillate overhead at a head temperature of 76.5° C/0.3 mm mercury. Distillation is terminated when the pot temperature reaches 185° C.

The light yellow distillate is verified to be N-(2-methoxyethyl)ethanamide via nuclear magnetic resonance (NMR) and infrared (IR) spectroscopy and via mass spectrometry. The 165.2 g portion of the distillate recovered is found to be about 95 percent pure via gas chromatography and therefore represents a 67 percent yield based on the moles of 2-methyl-2-oxazoline initially charged.

Example 2

Preparation of N-(2-methoxyethyl)ethanamide and 2-Methoxyethyl Amine from 2-Methyl-2-oxazoline and Methanol in the Presence of Lithium Methoxide.

A 127.6 g portion (1.5 moles) of 2-methyl-2-oxazoline is mixed with 192.0 g (6.0 moles) absolute methanol and 11.4 g (0.3 mole) lithium methoxide in a one-liter stainless steel Parr reactor equipped with a turbine stirrer. The reactor is sealed and heated, with stirring, to between 160° C and 165° C and 220 psig. The reaction is continued under those conditions for a period of 23.5 hours. Samples are periodically taken from the reactor through a dip-pipe which is below the liquid level. Analysis of these samples by gas chromatography with an internal standard indicates that, at 60–75 percent oxazoline conversions, corresponding amide yields are very high (95–100 percent) based upon the amount of oxazoline converted. At higher oxazoline conversions, a significant by-product appears, which is identified as 2-methoxyethylamine. The concentration of this amine levels out, and at 96.4 percent methyl oxazoline conversion, an 82.3 percent yield of 2-methoxyethylacetamide and an 11 percent yield of 2-methoxyethylamine results. Thus, yields of amide and amine, based on a 96.4 percent oxazoline conversion, are 93.3 percent.

Example 3

Preparation of N-(2-ethoxyethyl)propanamide and 2-Ethoxyethyl Amine from 2-Ethyl-2-oxazoline and Ethanol in the Presence of Lithium Methoxide.

A 99.1 g portion (1 mole) of 2-ethyl-2-oxazoline is mixed with 184 g (4 moles) anhydrous absolute ethanol and 6.6 g (0.17 mole) lithium methoxide in a one-liter stainless steel Parr reactor equipped with a turbine stirrer. The reactor is sealed and heated, with stirring, to about 165° C. The reaction is continued under those conditions for a period of 36.5 hours. Samples are periodically taken through a dip-pipe which is below the liquid level. Analysis of these samples by gas chromatography at the end of the 36.5 hour reaction period indicates that about 43 percent of the 2-ethyl-2-oxazoline has been consumed. The yield of N-(2-ethoxyethyl)propanamide is found to be about 34 percent based upon the 2-ethyl-2-oxazoline charged to the reactor. The yield of N-(2-ethoxyethyl)propanamide based upon the amount of 2-ethyl-2-oxazoline consumed is found to be about 80 percent.

The reaction product also contains a small amount (about 0.07 mole) of 2-ethoxyethylamine. Thus the combined yield of amide and amine is about 41 percent based upon the 2-ethyl-2-oxazoline charged to the reactor and about 96 percent based upon the amount of 2-ethyl-2-oxazoline consumed.

While the present invention has been described with reference to particular embodiments and examples, it will be understood that these embodiments are not intended to limit the scope of the instantly claimed invention.

What is claimed is:

1. A process for the preparation of an N-(2-alkoxyethyl)alkanamide of the formula

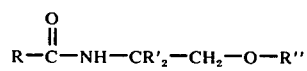

comprising reacting by contacting, in liquid phase, an oxazoline of the formula

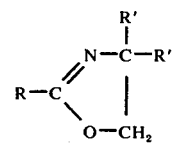

with an alkanol of the formula R"OH in the presence of a catalytic amount of an alkali metal or derivative thereof; wherein R is hydrogen or an alkyl radical containing from 1 to about 17 carbon atoms; each R' independently is hydrogen, methyl or ethyl; R" is methyl or ethyl.

2. A process of claim 1 wherein R is hydrogen, methyl or ethyl.

3. A process of claim 2 wherein R' is hydrogen.

4. A process of claim 3 wherein R is methyl or ethyl.

5. A process of claim 1 wherein the alkanol is methanol.

6. A process of claim 1 wherein the catalyst is selected from the group consisting of lithium, sodium, potassium and derivatives thereof corresponding to the formula $M^{+-}OR'''$ wherein M is lithium, sodium or potassium and R''' is hydrogen or an alkyl radical containing from 1 to about 4 carbon atoms.

7. A process of claim 6 wherein the catalyst is selected from the group consisting of lithium, sodium, potassium and methoxides and ethoxides thereof.

8. A process of claim 1 wherein the temperature is between about 100° C and about 225° C.

9. A process of claim 8 wherein the temperature is between about 150° and about 170° C.

10. A process of claim 1 wherein: the oxazoline is 2-methyl-2-oxazoline or 2-ethyl-2-oxazoline; the alkanol is methanol; the catalyst is sodium methoxide, present in an amount between about 1 and about 50 mole percent based on the oxazoline; the temperature is between about 100° C and about 225° C; and the pressure is superatmospheric or autogenous.

11. A process for the preparation of a 2-alkoxyethyl amine of the formula, $NH_2-C(R')_2-CH_2-O-R''$, comprising hydrolysis of an N-(2-alkoxyethyl)alkanamide prepared pursuant to the process of claim 1, wherein each R' independently is hydrogen, methyl or ethyl and R" is methyl or ethyl.

12. A process for the preparation of a 2-alkoxyethyl amine of the formula, $NH_2-C(R')_2-CH_2-O-R''$, comprising continuing to conduct the process of claim 1 in the presence of excess alkanol beyond the point at which no significant further increase in N-(2-alkoxyethyl) alkanamide concentration is observed.

* * * * *